US006762160B2

(12) United States Patent
Barbeau et al.

(10) Patent No.: US 6,762,160 B2
(45) Date of Patent: Jul. 13, 2004

(54) COMPOSITION FOR REMOVING BIOFILMS COMPRISING A DETERGENT AND A SALT FORMING ACID

(75) Inventors: Jean Barbeau, Montreal (CA); Denis Gravel, Saint-Lambert (CA); Abdelkrim Habi, Anjou (CA)

(73) Assignee: Universite de Montreal, Montreal (CA)

( * ) Notice: Subject to any disclaimer, the term of this patent is extended or adjusted under 35 U.S.C. 154(b) by 0 days.

(21) Appl. No.: 09/851,802

(22) Filed: May 9, 2001

(65) Prior Publication Data

US 2002/0016278 A1 Feb. 7, 2002

Related U.S. Application Data

(63) Continuation-in-part of application No. 09/187,249, filed on Nov. 6, 1998, now abandoned.

(51) Int. Cl.[7] .............................................. C11D 17/00
(52) U.S. Cl. ...................... 510/161; 510/199; 510/370; 510/386; 510/434
(58) Field of Search ................................. 510/161, 199, 510/370, 386, 426, 434, 492; 435/18

(56) References Cited

U.S. PATENT DOCUMENTS

| | | |
|---|---|---|
| 3,941,696 A | 3/1976 | Melnick et al. |
| 3,969,498 A | 7/1976 | Catania et al. |
| 4,115,293 A | 9/1978 | Schoenholz et al. |
| 4,391,287 A | 7/1983 | Konoshima |
| 4,448,750 A | 5/1984 | Fuesting |
| 4,526,751 A | 7/1985 | Gartner |
| 4,545,956 A | 10/1985 | Ciszewski et al. |
| 4,738,840 A | 4/1988 | Simon et al. |
| 4,770,884 A | 9/1988 | Hill et al. |
| 4,839,080 A | 6/1989 | Jungermann et al. |
| 4,898,681 A | 2/1990 | Burton |
| 4,923,809 A | 5/1990 | Otsuji et al. |
| 4,933,179 A | 6/1990 | Allison et al. |
| 4,961,923 A | 10/1990 | Heyde |
| 4,976,969 A | 12/1990 | Plamondon |
| 5,008,030 A | 4/1991 | Cook et al. |
| 5,038,769 A | 8/1991 | Krauser |
| 5,049,299 A | 9/1991 | Bunczk et al. |
| 5,118,430 A | 6/1992 | Rebouillat et al. |
| 5,165,503 A | 11/1992 | Hoffman |
| 5,227,161 A | 7/1993 | Kessler |
| 5,234,832 A | 8/1993 | Disch et al. |
| 5,280,042 A | 1/1994 | Lopes |
| 5,326,492 A | 7/1994 | Hodam, Jr. |
| 5,344,811 A | 9/1994 | Bunczk et al. |
| 5,370,534 A | 12/1994 | Wolf et al. |
| 5,460,833 A | 10/1995 | Andrews et al. |
| 5,486,304 A | 1/1996 | Eoga et al. |
| 5,622,708 A | 4/1997 | Richter et al. |
| 5,705,160 A | 1/1998 | Bruce et al. |
| 5,731,275 A | 3/1998 | Prevost et al. |
| 5,759,970 A | 6/1998 | Prevost et al. |
| 5,910,420 A | * 6/1999 | Tuompo et al. ............... 435/18 |

FOREIGN PATENT DOCUMENTS

| | | |
|---|---|---|
| EP | 109 279 | 5/1984 |
| EP | 0 293 040 | 11/1988 |
| EP | 0 313 527 | 4/1989 |
| WO | WO 92/13807 | 8/1992 |
| WO | WO 92/20228 | 11/1992 |
| WO | WO 94/00548 | 1/1994 |
| WO | WO 95/20366 | 8/1995 |
| WO | WO 96/20737 | 7/1996 |
| WO | 99/51578 | * 10/1999 |

OTHER PUBLICATIONS

1999, Patent Abstracts of Japan; vol. 1999, No. 8, Jun. 30, 1999, JP 11 061199A, Lion Corp.

1989, Stickler, D. et al. (1989) "Activity of Antiseptics against *Escherichia coli* Growing as Biofilms on Silicone Surfaces." Eur. J. Clin. Microbiol. Infect. Dis. vol. 8 No. 11: 974–978.

1994, Marchesi, J.R. et al. (1994). "SDS–degrading bacteria attach to riverine sediment in response to the surfactant or its primary biodegradation product dodecan–1ol." Microbiology, 140: 2999–3006.

1993, Ronner, A.R. and A.C.L. Wong (1993). "Biofilm Development and Santizer Inactivation of Listeria monocytogenes and *Salmonella typhimurium* on Stainless Steel and Buna–n Rubber." Journal of Food Protection, 56(9): 750–758.

1997, Barbeau, J. et al. (1997). "Biofilms in Dental Unit Waterlines: Ultrastructural and Cytochemical Analysis" Cells and Materials vol. 7, No. 2: 134–146.

1996, Barbeau, J. et al. (1996). "Multiparametric Analysis of Waterline Contamination in Dental Units" Applied and Environmental Microbiology vol. 62, No. 11: 3954–3959.

1997, Blanchard, A.P. et al. (1997). "Peroxygens in Biofilms, Community Interactions and Control" ed. J. Wimpenny, P. Handley, P. Gilbert, H. Lappin–Scott and M. Jones. Third Meeting of the British Biofilm Club, Powys, Sep. 26–28, 1997. p. 235–244.

1997, Chamberlain, A.H. L. (1997) "Biofilm Processes" In "Biofilms, Community Interaction and Control" ed. J. Wimpenny, P. Handley, P. Lappin–Scott and M. Jones. Third Meeting of the British Biofilm Club, Powys, Sep. 26–28, 1997. p. 41–46.

(List continued on next page.)

Primary Examiner—Necholus Ogden
(74) Attorney, Agent, or Firm—Merchant & Gould P.C.

(57) ABSTRACT

This invention relates to compositions for removing biofilms from contaminated surfaces. The compositions minimally comprise a detergent and a salt or a salt-forming acid. Preferably, the compositions comprise a detergent and a salt-forming acid, to provide salts and acids in equilibrium, in such a way that the biofilm is rapidly dismantled and removed in such an environment. The compositions may also comprise a bactericide, for destroying bacteria.

25 Claims, No Drawings

OTHER PUBLICATIONS

1994, Jacquelin, L.F. (1994). "Synergic de l'association d'enzymes ou de surfactanta et d'un desinfectant phenolique sur un biofilm bacterien". Pathologie Biologie. vol. 42. No. 5: 425–430. (Abstract in English).

1997, Stickler, D.J. (1997) "Chemical and Physical Methods of Biofilm Controls" In "Biofilms, Community Interactions and Control" ed. J. Wimpenny, P. Handley, P. Lappin–Scott and M. Jones. Third Meeting of the British Biofilm Club, Powys, Sep. 26–28, 1997. p. 215–225.

1997, Stoodley, P. et al. (1997) "Consensus Model of Biofilm Structures" In "Biofilms, Community Interactions and Control" ed. J. Wimpenny, P. Handley, P. Lappin–Scott and M. Jones. Third Meeting of the British Biofilm Club, Powys, Sep. 26–28, 1997. p. 1–9.

1997, Sutherland, I.W. (1997) "Exopolysaccharides Superglues or Velcro?" In "Biofilms, Community Interactions and Control" ed. J. Wimpenny, P. Handley, P. Lappin–Scott and M. Jones. Third Meeting of the British Biofilm Club, Powys, Sep. 26–28, 1997. p. 33–39.

1984, Whitacker, C et al. (1984). "Evaluation of Cleaning Strategies for Removal of Biofilms from Reverse–Osmosis Membranes" Applied and Environmental Microbiology, vol. 48, No. 3: 395–403.

1997, Wood, P. et al. (1997) "Surface Catalysed Hygeine" In "Biofilms, Community Interactions and Control" ed. J. Wimpenny, P. Handley, P. Lappin–Scott and M. Jones. Third Meeting of the British Biofilm Club, Powys, Sep. 26–28, 1997. p. 227–234.

* cited by examiner

COMPOSITION FOR REMOVING BIOFILMS COMPRISING A DETERGENT AND A SALT FORMING ACID

This application is a Continuation-in-part of Ser. No. 09/187,249, filed November 6, 1998, now abandoned.

FIELD OF THE INVENTION

This invention relates to solutions capable of efficiently cleaning surfaces susceptible to biofilm coating thereon. It further relates to a cleaning/disinfecting solution, comprising the cleaning components and a bactericidal effective amount of a disinfectant.

BACKGROUND OF THE INVENTION

Bacteria in natural aquatic environments have the marked tendency to interact with surfaces. The formation of surface biofilms can be regarded as a universal bacterial strategy for survival and for optimum positioning with regard to available nutrients. Bacteria growing in natural environments produce extensive exopolysaccharide (EPS) polymers that mediate both their attachment to surfaces and the formation of microcolonies and, eventually, the generation of biofilms. Biofilms are much more resistant to destruction than planktonic microorganisms. Although the mechanisms of this resistance are poorly understood, EPS are likely to play a role. In addition, biofilm bacteria are substantially resistant to surfactants, biocides and antibiotics. Two problems can arise from the presence of biofilms in a distributing aqueous system. First, the biofilm can clog pipes and tubings or interfere with the proper function of mechanical devices. Second, bacterial populations living in this protected mode of growth produce planktonic cells that contaminate fluids and alter their properties or, in the case of pathogens, can result in food poisoning or infections. It has also been proposed that biofilms could allow the multiplication of microbial pathogens stochasticly present in freshwater, as well as providing a mechanism for bioaccumulation of toxic substances. As a result, microbial biofilms constitute major industrial and medical concerns. These concerns are now being realized in the dental profession.

Dentists, dental surgeons and dental hygienists and their patients are well aware of the importance of meticulously sterilizing and disinfecting dental instruments. Indeed, since dental instruments are used directly in a patient's mouth, sometimes for invasive or surgical procedures, it is of paramount importance to minimize the presence of microorganisms carried by dental instruments. The microorganisms can range from relatively harmless bacteria to dangerous pathogens. Consequently, efforts are deployed to remove microorganisms from dental instruments and from the fresh water lines feeding dental instruments such as air/water seringes, high speed turbines, and ultrasonic scalers, or from saliva evacuation lines. For most hand held dental instruments, thermal sterilization remains one of the best methods for eradicating microorganism. However, thermal sterilization is obviously not practical for the decontaminating of fresh water lines which remain to this date difficult to rid of microorganisms.

It is well known in the dental profession that small diameter pipes carrying fresh water are contaminated by bacteria and other microorganisms contained in the water flowing through them (Barbeau et al. 1996). Some of the microorganisms inevitably adhere to the inner walls of the lines and accumulate together with microscopic sediments or other substances into what is commonly known as a biofilm (Barbeau et al. 1997). The biofilm quickly and tenaciously coats the inner walls of the lines and becomes a reservoir for the proliferation of microorganisms. Bacterial populations will rapidly reach alarming levels which will also be found in the water discharge from the dental instruments connected to the fresh water line. For example, the average bacteria count in the water discharge of dental instruments is known to be of approximately 200,000 colony forming units per milliliter (cfu/ml) and in some extreme cases can reach 10,000,000 cfu/ml (Barbeau et al. 1996).

Jacquelin et al. (Path. Biol. 42(5): 425–431 (1994)) disclose compositions comprising a detergent such as sodium dodecyl sulfate (SDS) or sodium deoxycholate (SDC) and a phenolic disinfectant. The solutions are not efficient to remove and/or destroy biofilms as seen from the photographs of FIG. 1 and from the concluding remarks of this reference.

Whittaker et al. (Appl. and Env Microbiol. 43(3): 395–403 (1984)) disclose a plurality of compositions tested for their cleaning/disinfecting properties against micoorganisms. Their best composition was SDS/urea, which was efficient on chlorine-treated osmosis membranes after 11 days of treatment, which time is far from being a practical cleaning/disinfecting time for dentistry.

European patent publication 109 279 describes a solution comprising a plurality of essential ingredients for sterilizing surgical apparatuses. Although this reference suggests that biofilm decontamination is contemplated, there is no demonstration whatsoever on that specific issue. Moreover, there is no teaching of any subset of combined ingredients which would be capable by itself to remove the biofilm, and optionally, to kill the embedded bacteria.

A commercially available mouthwash sold under the trademark PLAX which comprises SDS 0.25%, sodium benzoate 2% and sodium salicylate 0.2%, supposedly helps in removing dental plaque prior to tooth brushing. The efficacy of this solution against biofilms in general is however doubtful given the short time of contact within which dental plaque is to be removed, even when tooth brushing follows.

Patent publication WO 96/20737, assigned to the present proprietor, describes compositions capable of cleaning and disinfecting biofilm-coated surfaces. These compositions comprise SDS 1%–2%, hydrogen peroxide 5%, EDTA 1%, mandelic and lactic acids in individual 1% concentration or in combined 2% concentration (mandelic acid being a bactericide). They further describe sub-compositions comprising the same concentrations of SDS/hydrogen peroxide/EDTA and SDS/acids. There is no teaching in these publications of compositions which would be different therefrom and still equivalent thereto, and there is no teaching of how specific components attack the integrity of the biofilms e.g. there is no mechanism of action proposed which would lead to establish a generic class of components useful for the purpose of removing biofilms with high efficacy.

Accordingly there still remains a need for compositions for cleaning biofilm-coated surfaces which will effectively dislodge a biofilm and optionally kill the microorganism flora in the dislodged biofilm, these compositions being adapted upon a variety of industrial uses and needs.

SUMMARY OF THE INVENTION

Against all expectations and documented evidence, the present inventors found that effective removal of biofilm may be achieved, using a solution minimally comprising a detergent and acids which, at the working pH, form salts in a substantial proportion. These two components by themselves are sufficient to remove well-established biofilms in a period of time varying from within 1 hour to an indefinite time, more preferably between about 1 hour and 18 hours.

When destruction of microorganisms is a concern, particularly in the medical or dental professions, a bactericide must be added to the solution. The bactericide contacts the surface rid of biofilm and wherein residual microorganisms retained on the surface will be killed. Preferably, the disinfecting and cleaning actions are allowed to occur concurrently.

In accordance with the present invention is provided a solution for dislodging a biofilm from a surface, which comprises an effective dislodging amount of a detergent and an effective dislodging amount of a salt or of an acid which forms a salt at a working pH value, or both, said salt being capable of displacing divalent cations present in the structure of the biofilm with the proviso that the composition is neither a mixture of SDS 1%–2% and EDTA 1%, a mixture of SDS 1%–2% and mandelic and lactic acids, each at an individual concentration of 1% or in a combined concentration of 2%, nor a mixture of SDS 0.25%, sodium salicylate 0.2% and sodium benzoate 2% (PLAX), all percentages representing final weight per volume concentrations.

The acid or salt is preferably an organic acid or salt. The components of the solution would preferably exclude components that comprise or produce an oxidant namely an oxygen-producing species such as peroxide or a chlorine-producing species such as sodium hypochlorite.

The components of the solution would preferably exclude a bactericide which is a terpene known from WO 93/17558.

Despite the fact that some components are excluded from the compositions of this invention, the use of all these compositions including the disclaimed ones for their capacity to remove biofilm is within the scope of the present invention.

It is another object of this invention to provide a composition for dislodging and destroying a biofilm, which further comprises a bactericide although it excludes the above-disclaimed bactericides.

In preferred embodiments, the detergent is SDS in a concentration excluding the above disclaimed species of at least about 0.1% or any detergent having a biofilm dislodging potency substantially equivalent thereto. The acid is mandelic acid in a concentration of at least about 0.1% at a working pH value (pH 5 is one example), or a mandelate salt, or any acid or salt having a biofilm dislodging potency substantially equivalent thereto at a suitable working pH. For example, the salt or acid may interestingly be an EDTA salt or acid in a concentration of at least about 0.25% at a working pH value. At pH 5, EDTA acid forms EDTA salt and is performing when combined to SDS, with or without any other acid, although better results were obtained with another acid.

In more preferred embodiments, the acid is selected from the group consisting of mandelic, 2-ketoglutaric, acetic, iminodiacetic, mucic, glycolic, fumaric, lactic, aspartic, phosphoric, pyruvic, chloroacetic, oxalic, citric, oxamic, malic, dichloroacetic, phenylacetic, benzylic, maleic, succinic, chloromandelic, glutamic, nitrilotriacetic, boric, adipic, formic, glucuronic, salicylic, benzoic, benzoyl formic, phthalic, ketopimelic acids, alanine, serine, tryptophan, tyrosine, bicine, tricine and glycine. Except for phosphoric acid, all these preferred acids are organic acids. When a bactericidal activity is needed, a bactericide such as hydrogen peroxide or any bactericide having a bactericidal potency substantially equivalent thereto may be added. Other bactericides like phenol derivatives or sodium hypochlorite are examples of good bactericides. They have been used in concentrations of at least 0.1% and 0.5%, respectively. In even more preferred embodiments, the composition further comprises biofilm dislodging enhancer agents such as chaotropic agents or calcium chelators.

A calcium chelator such as EDTA, preferably in a salt form, in a concentration of at least about 0.25% or any calcium chelator having a chelating potency substantially equivalent thereto may be added.

A chaotropic agent such as SDS in a concentration of at least about 0.1% or any chaotropic agent having a chaotropic potency substantially equivalent thereto may also be added.

In more preferred embodiments, the compositions comprise at least about 0.1% SDS, at least about 0.1% acid, at least about 0.25% EDTA, the acid being selected from the group consisting of 2-ketoglutaric, acetic, iminodiacetic, mucic, glycolic, fumaric, aspartic, phosphoric, pyruvic, chloroacetic acids and alanine.

In a mostly preferred embodiment, the compositions comprise at least about 0.1% but less than 1% SDS, about 0.1%–2% acid, and at least about 0.25% but less than 1% EDTA, the acid being mandelic acid or any other of 2-ketoglutaric, acetic, iminodiacetic, mucic, glycolic, fumaric, aspartic, phosphoric, pyruvic, chloroacetic acids and alanine.

The highest concentrations confer a strength to the composition such as it is effective within one hour. The lowest concentrations confer a good performance within 18 hours.

Good bactericides comprise hydrogen peroxide about 5%, or phenol derivatives at least about 0.1%, or sodium hypochlorite at least about 0.5% These bactericides are tuberculocides e.g. they are active against Mycobacterium spp. which are resistant to a large panel of bactericides.

DESCRIPTION OF THE PREFERRED EMBODIMENTS OF THE INVENTION

Each component tested in this application will be given an abbreviated name, which complete definition is as follows:

| | |
|---|---|
| SDS | Sodium dodecyl sulfate |
| EDTA | Ethylenediamine tetraacetic acid |
| $H_2O_2$ | Hydrogen peroxide |
| CPC | Cetylpyridinium chloride |
| Tween 20 | Polyoxyethylene sorbitan monolaurate |
| SCS | Sodium cocoyl sarcosinate |
| SLS | Sodium lauryl sarcosinate |
| SDDD | Sodium n-decyl diphenylether disulfonate |
| HEEDTA | N-(hydroxyethyl)ethylenediamine triacetic acid |
| DTPA | Diethylenetriamine pentaacetic acid |

Starting from the solutions already described in the patent publication WO 96/20737 assigned to the same proprietor, comprising SDS 1%–2%/mixture of mandelic and lactic acids 2%/EDTA 1%/hydrogen peroxide 5%, we first replaced mandelic and lactic acids with a plurality of acids used individually in 1% concentration (w/v), the pH of the working solution being brought to 5.0. We further tried different components with hope to find equivalents for each other essential and non-essential ingredients of the composition.

The compositions were allowed to contact biofilms for 1 and 18 hours to evaluate their cleaning and disinfecting efficacy.

Testing the Disinfectant.
Optical and Scanning Electron Microscopy.

Two-cm long pieces of dental unit waterlines tubings were used. These tubings were taken from functional dental units installed at the faculty of dentistry of the University of Montreal. Our previous studies (1992–1996) have shown that the lumen of these tubings is covered with mature biofilms. The pieces were sectioned longitudinally with a sterile scalpel blade to expose the biofilm. Another series of tubings was left untouched. Sections of tubings were placed in sterile 5 ml disposable test tubes containing solutions to be tested.

After 1 or 18 hours without agitation at room temperature, tubings were rinsed three times with sterile water. Examination was done first with a binocular microscope at a magnification of 40×. Data were recorded on a arbitrary scale by two different examiners and noted as from 4+(same as control) to 0 (no biofilm).

Selected pieces of tubings were processed for electron microscopy.

Scanning Electron Microscopy (SEM)

For SEM observations, following fixation, post-fixation and dehydration, samples were critical point dried with carbon dioxide in a Balzers CPD 030 Critical Point Dryer (Balzers, Furstentum, Liechtenstein), then mounted with a conductive carbon paint on aluminum stubs and sputtered with gold, or carbon-evaporated in a Bal-Tec MED 020 High Vacuum Coating System (Bal-Tec Products Inc., Middlebury, Conn., USA). The interior of tubing segments was examined with a field emission JEOL JSM 6300F SEM operated at an accelerating voltage of 15 kV. The gold-coated specimens were used for SEI while the carbon-coated ones were visualized by BEI.

Antibacterial Activity.

To test the antibacterial activity, we used the same setup as above. After the 1 or 18 hour incubation, tubings were rinsed with sterile water. Pieces of tubings were dropped in sterile test tubes containing 4 ml of R2Am medium. Test tubes were capped and incubated for 7 days at room temperature. These conditions proved to be best for the growth of the majority of dental unit waterlines bacteria. Data were recorded as presence or absence of growth with a spectrophotometer at $\lambda$=590 nm.

We have isolated 30 strains of DUWL bacteria among which, *P. aeruginosa*, *P. putida*, *M. mesophilicum*, *A. calcoaceticus*, *P. fluorescens* were the most frequent species. We tested these strains individually in the disinfectant. Pure culture of bacteria in liquid R2Am broth were used.

In Situ Testing.

The disinfectant was tested in the ACCM© prototype in a closed room at the Faculty. The ACCM was installed on a A-dec dental unit by one of our technicians. Before the study, water samples were taken for bacterial counts, and a two-cm piece of the air/water syringe hose was taken for SEM. The lines were filled with disinfectant containing alizarin green as an indicator and the setup was left unused overnight. The next day, the disinfectant was drained until no coloration was seen. Draining was done for an extra 2-min and a 4-ml water sample was taken for bacterial counts. Another 2-cm piece of tubing was sectioned for SEM. A second sample was taken at the end of the day and the lines were filled with disinfectant for 18 hours. This routine was repeated over a period of one month. In some experiments, the disinfectant was left to react for 1 hour in lieu of 18 hours.

Collection and Plating of Water Samples.

All the water samples were vigorously agitated with a vortex for 15 seconds. The plating was done by inoculating Petri dishes with 100 $\mu$l of a 1:10, 1:100 and 1:1000 dilution in duplicate, or by using an automatic spiral plating system (Meyer Service & Supply, Ontario, Canada) after a tenfold dilution of the sample. The enumeration was done using a magnifying glass and a counting grid.

Control samples (20 ml) were obtained from nearest taps in each clinic and at the source upstream to the connection to the dental unit in selected units. These samples were filtered through a 25 mm polycarbonate filter (0.22 $\mu$m) (Millipore, Montréal, Canada) using a sterile syringe and a filter holder (Millipore). The filters were then placed on the surface of the culture medium in a Petri dish and incubated.

Newly installed dental units (Kavo, Germany) at the dental school were also sampled just before their first clinical use with the same sampling technique.

Culture Conditions.

A modification of the medium of Reasoner (termed R2Am) was used. The composition is as follows: starch 0.5 g, yeast extract 0.5 g, trypticase peptone 0.5 g, dextrose 0.5 g, $K_2HPO_4$ 0.3 g, $MgSO_4$ 0.05 g, succinate 0.25 g, casamino acids 0.5 g, agar 7.5 g, and distilled water to 1L. Tryptone soy agar and Sheep blood agar (Difco, Montréal, Canada) were also used. Bacteria were cultivated in aerobiosis and anaerobiosis (10% $CO_2$, 10% $H_2$ and 80% $N_2$, anaerobic cabinet: Forma Scientific, Montréal, Canada) for the determination of their dependency on oxygen and at 25° C. and 37° C. over time between 24 and 480 hours.

Acid Substitutions:

We first substituted a plurality of acids for mandelic and lactic acids. All these acids were used in 1% (w/v) final concentration. Results are shown in Table 1.

TABLE 1

ACIDS SUBSTITUTING FOR MANDELIC OR LACTIC ACIDS

| Selected Acid (1%) | DESCRIPTION | | | | RESULTS AFTER DISINFECTION | | |
|---|---|---|---|---|---|---|---|
| | $H_2O_2$ | EDTA | SDS | pH | 1 hour | 18 hours | Growth |
| Mandelic Acid | 5% | 1% | 1% | 5,0 (NaOH 10%) | − | − | − |
| Lactic Acid | 5% | 1% | 1% | 5,0 (NaOH 10%) | + | + | − |
| D-Tartric acid | 5% | 1% | 1% | 5,0 (NaOH 10%) | ++ | ++ | − |
| Citric Acid | 5% | 1% | 1% | 5,0 (NaOH 10%) | +++ | + | − |
| Oxalic Acid | 5% | 1% | 1% | 5,0 (NaOH 10%) | ++ | + | − |
| Oxamic Acid | 5% | 1% | 1% | 5,0 (NaOH 10%) | +++ | + | − |
| Sulfamic Acid | 5% | 1% | 1% | 5,0 (NaOH 10%) | +++ | ++ | − |
| Malonic Acid | 5% | 1% | 1% | 5,0 (NaOH 10%) | ++ | ++ | − |
| Malic Acid | 5% | 1% | 1% | 5,0 (NaOH 10%) | + | + | − |
| Dichloroacetic Acid | 5% | 1% | 1% | 4,99 (AcOH) | + | + | − |

TABLE 1-continued

ACIDS SUBSTITUTING FOR MANDELIC OR LACTIC ACIDS

| | DESCRIPTION | | | | RESULTS AFTER DISINFECTION | | |
|---|---|---|---|---|---|---|---|
| Selected Acid (1%) | $H_2O_2$ | EDTA | SDS | pH | 1 hour | 18 hours | Growth |
| 2-Ketoglutaric Acid | 5% | 1% | 1% | 5,0 (NaOH 10%) | − | − | − |
| Maleic Acid | 5% | 1% | 1% | 5,0 (NaOH 10%) | + | + | − |
| Succinic Acid | 5% | 1% | 1% | 5,0 (NaOH 10%) | + | + | − |
| Acetic Acid | 5% | 1% | 1% | 5,0 (NaOH 10%) | − | − | − |
| Phenylacetic Acid | 5% | 1% | 1% | 5,0 (NaOH 10%) | ++ | + | − |
| R-Chloromandelic Acid | 5% | 1% | 1% | 5,0 (NaOH 10%) | + | + | − |
| L-Serine | 5% | 1% | 1% | 5,0 (AcOH) | + | + | − |
| D-Phenylalanine | 5% | 1% | 1% | 5,0 (HCl 10%) | ++ | ++ | − |
| Glutamic Acid | 5% | 1% | 1% | 5,0 (NaOH 10%) | + | + | − |
| R-2-Phenylglycine | 5% | 1% | 1% | 5,0 (AcOH) | ++ | ++ | − |
| Glycine | 5% | 1% | 1% | 5,0 (AcOH) | ++ | ++ | − |
| Benzilic Acid | 5% | 1% | 1% | 5,0 (NaOH 10%) | ++ | + | − |
| Iminodiacetic Acid | 5% | 1% | 1% | 5,0 (NaOH 10%) | − | − | − |
| Nitrilotriacetic Acid | 5% | 1% | 1% | 5,0 (NaOH 10%) | + | + | − |
| Tricine | 5% | 1% | 1% | 5,0 (AcOH) | +++ | + | − |
| Bicine | 5% | 1% | 1% | 5,0 (AcOH) | ++ | + | − |
| Mucic Acid | 5% | 1% | 1% | 5,0 (NaOH 10%) | − | − | − |
| L-Aspartic Acid | 5% | 1% | 1% | 5,0 (NaOH 10%) | + | − | − |
| L-Ascorbic Acid | 5% | 1% | 1% | 5,0 (NaOH 10%) | ++++ | +++ | − |
| Phosphoric Acid ($H_3PO_4$) | 5% | 1% | 1% | 5,0 (NaOH 10%) | ++ | − | − |
| Boric Acid ($B(OH)_3$) | 5% | 1% | 1% | 4,99 (AcOH) | + | + | − |
| Pyruvic Acid | 5% | 1% | 1% | 5,0 (NaOH 10%) | ++ | − | − |
| Glycolic Acid | 5% | 1% | 1% | 5,0 (NaOH 10%) | − | − | − |
| Adipic Acid | 5% | 1% | 1% | 5,0 (NaOH 10%) | + | + | − |
| Formic Acid | 5% | 1% | 1% | 5,0 (NaOH 10%) | +++ | + | − |
| Glucuronic Acid | 5% | 1% | 1% | 5,0 (NaOH 10%) | + | + | − |
| Salicylic Acid | 5% | 1% | 1% | 5,0 (NaOH 10%) | ++ | + | − |
| Benzoic Acid | 5% | 1% | 1% | 5,0 (NaOH 10%) | + | + | − |
| Benzoylformic Acid | 5% | 1% | 1% | 5,0 (NaOH 10%) | + | + | − |
| Chloroacetic Acid | 5% | 1% | 1% | 5,0 (NaOH 10%) | + | − | − |
| Phthalic Acid | 5% | 1% | 1% | 5,0 (NaOH 10%) | + | + | − |
| Fumaric Acid | 5% | 1% | 1% | 5,0 (NaOH 10%) | − | − | − |
| Ketopimelic Acid | 5% | 1% | 1% | 5,0 (NaOH 10%) | + | + | − |
| L-Tryptophan | 5% | 1% | 1% | 5,0 (AcOH) | + | + | − |
| DL-Alanine | 5% | 1% | 1% | 5,0 (AcOH) | + | − | − |
| DL-Tyrosine | 5% | 1% | 1% | 5,0 (AcOH) | + | + | − |

Scale evaluation:
−: no biofilm and ++++: no significant removal of film.

To our surprise, all the tested acids manifested a capacity to dislodge biofilms, leaving the biofilm constituents free for the bactericidal activity of hydrogen peroxide. Some acids conferred a slow but nevertheless significant tendency of the solution to dislodge biofilms with time, while the others were more rapid in this respect. We have selected cleaning solutions capable of performing at practical times: 1 hour or less, and overnight (about 12–18 hours). From the above list, seven acids were performing within less than 1 hour: mandelic, 2-ketoglutaric, acetic, iminodiacetic, mucic, glycolic and fumaric acids. To this restricted list of very performing acids can be added those acids performing between 1 and 18 hours: lactic, aspartic, phosphoric, pyruvic, chloroacetic acids and alanine. Since the above results are of semi-quantitative nature only, we add to the list of acceptably performing acids: oxalic, citric, oxamic, malic, dichloroacetic, phenylacetic, benzylic, maleic, succinic, chloromandelic, glutamic, nitrilotriacetic, boric, adipic, formic, glucuronic, salicylic, benzoic, benzoylformic, phthalic, ketopimilic acids as well as serine, tryptophan, tyrosine, bicine, tricine and glycine, because they all led to sufficient decontamination within the specified times. All the other acids can be used when time is not a major concern or when mechanical brushing is used to accelerate removal of biofilm. It is worthwhile noting the isomeric form of an acid does not appear to influence its dislodging capabilities.

Taking the results of acid substitution altogether, it appeared clear that the common point between the acids was that they may form salts at the working pH of 5.0.

These observations led us to appreciate why the sub-compositions already published by the present assignee minimally comprising SDS/acids were performing cleaning and disinfecting solutions. The presence of the detergent and salt forming acids is most probably responsible for breaking the integrity and dislodging the biofilm. Since mandelic acid is also a bactericide, the combination SDS/acids was also an efficient detergent/disinfectant solution.

Further, the other sub-compositions disclosed in the same patent publications minimally comprising SDS/EDTA/hydrogen peroxide, which were also performing sub-combinations revealed that EDTA used as a salt was capable of complementing SDS in the cleaning component of the solution. Hydrogen peroxide had the role of the bactericide.

It is therefore an object of this invention to provide a minimal cleaning solution comprising a detergent and a salt forming acid (direct addition of salts in the solution is also an option). The bactericides are added in the solutions, when a bactericidal complement is desired. Any bactericide may be added to the above cleaning solution, which would have for effect to confer an additional disinfecting action thereto, which action is greatly facilitated by the dislodging action of the cleaning ingredients: detergent and salts. Amongst the bactericides tested, sodium hypochlorite, phenol derivatives and hydrogen peroxide showed a broad host killing activity, even against Mycobacterium sp. known for their high level of resistance towards bactericides. Mandelic acid has a dual role as a salt forming acid and as a bactericide. Povidone-iodine was also tested and had a significant efficiency when combined to the detergent Tween 20™. All the above bactericides are non limitative examples of bactericides.

Equivalents:

The above Table I shows that many acids are equivalent to mandelic and lactic acids.

Different types of detergents have been tried, a cationic one (cetylpyridinium (CPC), also a bactericide), non-ionic ones (Tween 20™ and povidone-iodine, also a bactericide) and anionic ones (SDS, SCS and SDDD). All these detergents were capable of dislodging biofilms. SDS was the preferred one. SDS achieved very good activity even at a concentration as low as 0.15% after one hour, and a perfect efficiency at the same concentration after 18 hours. It is worthwhile noting that the solution tested with 0.15% SDS also contained 6% hydrogen peroxide, and low amounts of HEEDTA (acid; 0.3%), acetic acid (0.1%) and zinc sulfate heptahydrate (0.1%). This solution corresponds to the best one described in EP 109 279. The pH of the solution was adjusted from 2.42 to pH 5, which entails of salt formation.

Further, the commercial mouthwash PLAX™, comprising 0.25% SDS, 2% sodium benzoate and 2% sodium salicylate (pH 7.35) showed good biofilm removal, although not perfect, after 18 hours of contact. The acceptable performance of that solution confirms that salts only may be used although the presence of acid(s) appears optimal. The effect of PLAX also confirms that a bactericide such as hydrogen peroxide is not necessary in the biofilm removal.

The above results show that the concentration of detergent and salts may be quite low if the time of contacting is longer (for example overnight), while higher concentrations confer more strength and decrease the time necessary for dislodging biofilms (within 1 hour for example).

Enhancers:

As mentioned above, we already described sub-combinations which were as efficient as the complete combination SDS 1%–2%/EDTA 1%/hydrogen peroxide 5%/mandelic and lactic acids 2%. These sub-combinations comprise the ingredients SDS/EDTA/hydrogen peroxide and SDS/acids. In both cases, sub-compositions comprise the ingredients detergent and bactericide. What was not explained at the time was why EDTA was essential to the first sub-composition to perform well. The above results provide such an explanation: EDTA salts greatly improve the dislodging or cleaning capacity of the solutions. The presence of EDTA is no longer deemed necessary to present cleaning solutions, since EDTA may be replaced by other salts or salt forming acids. EDTA is rather considered as an activity enhancer, because this compound is also a good divalent ion chelator, and as such, it may help in withdrawing Ca2+ ions from the polysaccharide biofilm matrix, leading to a faster dismantlement thereof.

SDS was the preferred detergent and it is further worthwhile noting that this detergent is also a chaotropic agent. It is therefore contemplated that a chaotropic agent may be optionally added to increase the biofilm dislodging strength of the solution. Such chaotropic agents include but are not limited to SDS, urea and guanidine. The chaotropic agent is also considered as an optional activity enhancer.

Additives:

Should the detergent used in the composition produce foam, it might be desirable to add an anti-foamer. Also, a dye might be added to the compositions of this invention for easy monitoring of the extent of rinsing. Further, flavors or scents may be added to provide a pleasant taste or smell to surfaces to be cleaned.

Fresh water lines supplying dental instruments are of a very small diameter, which excludes the possibility of scrubbing. This would not be the case for dentures, surfaces or tubings of larger diameter. The compositions of the present invention have the advantage of showing efficient decontamination in the complete absence of scrubbing in a convenient time of decontamination. The present invention is not only useful for dental instruments or protheses. It will become obvious that it is intended for other applications, e.g. cleaning or decontaminating any type of tubing or container on the surface of which microorganisms are adsorbed and form a biofilm. In such other applications, scrubbing or any other mechanical aid is not at all excluded. Should these compositions be used in pipes of a larger diameter and length, for example, wherein a non-cost effective large volume of cleaning solution would be needed to fill the pipes, it is possible that a mechanical action would help in the action of the solution. A mechanical aid, when envisaged, would help in reducing the duration of cleaning and/or in spreading the cleaning solution on a surface. It is further not excluded to add a vehicle allowing the cleaning solution to stay in contact with the surface to be decontaminated as long as possible. Some or all of cleaning solution components might be delivered in separate vials, in concentrated forms, to be admixed in the final reconstituted volume. This could reduce the handling and storage of large volumes of decontaminating solutions when they are used for cleaning large surfaces.

Minimal and Optimal Effective Concentrations of Components

Detergents:

SDS has been tried at a final concentration of 0.15% (w/v) and did work well within one hour. So, SDS certainly can be as low as about 0.1% when the duration of treatment may last about one hour or more. The most preferred SDS concentration was 1% which achieved a perfect cleaning efficacy within one hour. Any detergent at a concentration as potent as at least about 0.1% SDS is within the scope of this invention. For example, the following detergents and concentrations have been tried with success:

SDDD 0.015%–1%,

SCS 0.3%–1%,

Tween 20™ 4%, and

CPC 0.1%–0.5%.

So, detergents of all classes: non-ionic, anionic and cationic, have been all successful in removing biofilms, and this invention should not be limited to the tested five detergents.

Salt-Forming Acids:

Mandelic acid has been tried with success in a concentration extending from 1% to 10%. Besides that, acetic acid has been tried in a range of concentrations 0.1% to 1% and was very efficient. Further, a plurality of acids (1%) may substitute for mandelic acid 1% (see Table 1). It is therefore contemplated that acids can be used in a minimal concentration of about 0.1% at a salt-forming pH. Preferred acid concentration is 1% for rapidly acting solutions, with reference to mandelic acid. Any acid capable of forming salts at the working pH, in concentrations equipotent to at least about 0.1% mandelic acid, depending on the desired contacting time, is within the scope of this invention. Although a pH of about 5 has been tested, it is readily apparent to a skilled reader that the pH of the solutions is not restricted to that value.

Cleaning Enhancers:
Chelators:

Tetrasodium EDTA (0.25%–1%) has been tried with a certain degree of success against biofilms. Any chelator in a concentration equipotent to the above concentrations of EDTA is within the scope of this invention. It is worthwhile noting that HEEDTA has been used in the acid form (0.3%) and was good when another salt forming acid: acetic acid, was at a concentration of 0.1% to 1% and when the pH was brought from 2.42 to 5.0. So, chelator salts can be used or chelator acid precursors can be used in salt forming conditions. It is recalled that the chelator is an optional component; it is used to increase the cleaning strength of the solution. Its function is mainly to capture divalent ions such as $Ca^{2+}$ which are involved in EPS integrity.

Chaotropic Agents:

SDS has a dual action as a detergent and a chaotropic agent. Since a plurality of non-chaotropic detergents may substitute for SDS, the chaotropic activity is not considered essential to the claimed compositions. However, since SDS was the preferred detergent, it is contemplated that a chaotropic agent may be useful, as an optional component, in increasing the cleaning strength of the solution. Any chaotropic agent having the potency of in a concentration of at least about 0.1% SDS is within the scope of this invention.

Bactericides:

When it is desirable to complete the cleaning solution with a bactericidal activity, especially in the medical field, a bactericide can be added in an effective concentration. It is recalled that bactericides alone are less effective against biofilms than against planktonic micoorganisms. However, when bactericides are combined to a detergent/salt solution, or contacted with surfaces thereafter, they are capable of killing microorganisms which are retrieved as planktonic organisms and no longer organized as a biofilm, due to the detergent/acid/salt effect. Povidone-iodine 10%, mandelic acid 1%, sodium benzoate/salicylate 2%/0.2%, hydrogen peroxide 5%, sodium hypochlorite 0.5%, phenol 0.1% and CPC 0.1% –0.5% have all been tried with success, which indicates that any bactericide may be added in the cleaning solution in so far as the selected bactericide has a killing activity against the populations of microorganisms to eliminate.

Amongst the above-listed bactericides, we have preferred hydrogen peroxide, sodium hypochlorite and phenol, because these bactericides qualify as tuberculocides; they are efficient against highly resistant Mycobacterium species and they have a large spectrum of efficiency against microorganisms. Table 1 shows that hydrogen peroxide really killed the bacteria, which translated into a total absence of growth after treatment.

Dismantling the Exopolysaccharides (EPS) Present in the Biofilms:

EPS exist in more or less ordered forms in natural environment. Many bacterial EPS appear to adopt a double helicoidal configuration and the association of the double helices is facilitated by ions (such as Ca2+) and by water molecules. The physical properties of EPS and hence of biofilms may be influenced by the presence of free anionic groups (uronic acids, phosphate groups, pyruvate ketals or succinyl half esters). Hydrogen bonding involving exposed hydroxyl groups can also be significant. Localized hydrophobic regions may also exert influence. Therefore interacting with the ions involved in the maintenance of cohesive biofilms is a target for the dismantlement thereof. It has been suggested that excess Na+ may exchange with Ca2+ and that local proton gradients may convert the salt form of the EPS to the proton form, again altering its properties. (I. W. Sutherland in "Biofilms, Community Interactions and Control" ed. J. Wim-Penny, P. Handley, P. Gilbert, H. Lappin-Scott and M. Jones. Third Meeting of the British Biolfim Club, Powys, September 1997).

Even if it may have been envisaged that changes in the ionic environment of a biofilm may alter its integrity, no one has ever come up with satisfyingly performing solutions, or when such solutions exist, there has been no teaching of using them for removing biofilms and this, without any mechanical aid. The present invention relates to compositions and methods minimally comprising or making use of salts or salt-forming acids and a detergent. Preferably, a salt-forming acid is used to create an equilibrium between acids and salts, both of which being involved in attacking the biofilm components. Such salts would include salts capable of dissociating from the counter anion. The preferred salts include compounds of group Ia, namely lithium, sodium and potassium. The detergent appears to have a synergistic effect in solubilizing the components and in exposing EPS sublayers which, in turn, become attackable by acids and salts. The present ingredients when combined are very efficient and achieve complete removal of biofilms. Bactericidal agents, when added, become efficient against biofilms, because the biofilm becomes disorganized and is no longer impermeable to the anti-microbials.

Although the present invention has been described herein above by way of preferred embodiment thereof, these embodiments can be modified at will without departing from the spirit and the nature of the subject invention. These modifications are within the scope of this invention as defined in the appended claims.

What is claimed is:

1. A composition for removing a biofilm from a surface, which does not produce or comprise a peroxide, a terpene or sodium hypochlorite, which comprises an effective dislodging amount of a detergent cetylpyridinium chloride (CPC) at a final concentration of at least 0.1%, and an effective dislodging amount of a salt or of an acid which forms a salt at a working pH value, or both, said salt or acid being different from said CPC and said salt or acid when combined to the CPC is capable of displacing divalent cations, dismantling and destroying the structure of said biofilm.

2. A composition as defined in claim 1, further comprising an effective amount of a bactericide.

3. A composition as defined in claim 1, wherein said acid is mandelic acid achieving a final concentration of at least 0.1%.

4. A composition as defined in claim 2, wherein said acid is mandelic acid achieving a final concentration of at least 0.1%.

5. A composition as defined in claim 1, wherein said salt or acid is an EDTA salt or acid achieving a final concentration of at least 0.25%.

6. A composition as defined in claim 2, wherein said salt or acid is an EDTA salt or acid achieving a final concentration of at least 0.25%.

7. A composition as defined in claim 1, wherein said salt is sodium mandelate formed from mandelic acid achieving a final concentration range of at least 0.1% at a working pH value adjusted to 5.

8. A composition as defined in claim 2, wherein said salt is sodium mandelate formed from mandelic acid achieving a final concentration range of at least 0.1% at a working pH value adjusted to 5.

9. A composition as defined in claim 1, wherein said acid is selected from the group consisting of mandelic, 2-ketoglutaric, acetic, iminodiacetic, mucic, glycolic, fumaric, lactic, aspartic, phosphoric, pyruvic, chloroacetic, oxalic, citric, oxamic, malic, dichloroacetic, phenylacetic, benzylic, maleic, mandelic, succinic, chioromandelic, glutarnic, nitrilotriacetic, boric, adipic, formic, ghicuronic, salicylic, benzoic, benzoyl formic, phthalic, ketopimelic acids, alanine, serine, tryptophane, tyrosine, bicine, tricine and glycine.

10. A composition as defined in claim 5, wherein said acid is selected from the group consisting of mandelic, 2-ketoglutaric, acetic, iminodiacetic, mucic, glycolic, fumaric, lactic, aspartic, phosphoric, pyruvic, chloroacetic, oxalic, citric, oxamic, malic, dichloroacetic, phenylacetic, benzylic, maleic, mandelic, succinic, chioromandelic, glutamic, nitrilotriacetic, boric, adipic, formic, glucuronic, salicylic, benzoic, benzoyl formic, phthalic, ketopimelic acids, alanine, serine, tryptophane, tyrosine, bicine, tricine and glycine.

11. A composition as defined in claim 2, wherein said bactericide is any bactericide having a bactericidal potency and host spectrum substantially equivalent to hydrogen peroxide.

12. A composition as defined in claim 2, wherein said bactericide is the same component as the acid mandelic acid.

13. A composition as defined in claim 12, wherein the mandelic acid, achieves a final concentration of at least 0.1%.

14. A composition as defined in claim 1, which further comprises a biofilm dislodging enhancer agent.

15. A composition as defined in claim 2, which further comprises a biofilm dislodging enhancer agent.

16. A composition as defined in claim 14, wherein said enhancer agent is a calcium chelator.

17. A composition as defined in claim 15, wherein said enhancer agent is a calcium chelator.

18. A composition as defined in claim 16, wherein said calcium chelator is the same component as the acid EDTA, which is used as the acid or as a salt of EDTA achieving a final concentration of at least 0.25%.

19. A composition as defined in claim 17, wherein said calcium chelator is the same component as the acid EDTA, which is used as the acid or as a salt of EDTA achieving a final concentration of at least 0.25%.

20. A composition as defined in claim 14 wherein said enhancer agent is a chaotropic agent.

21. A composition as defined in claim 15 wherein said enhancer agent is a chaotropic agent.

22. A composition for removing a biofilm from a surface, which does not produce or comprise a peroxide, a terpene or sodium hypochiorite, which comprises an effective dislodging amount of a detergent cetyloyridinium chloride (CPC) and an effective dislodging amount of a salt or of an acid which forms a salt at a working pH value; said acid being selected from the group consisting of mandelic, 2-ketoglutaric, acetic, iminodiacetic, mucic, glycolic, fumaric, lactic, aspartic, phosphoric, pyruvic, chioroacetic, oxalic, citric, oxamic, malic, dichioroacetic, phenylacetic, benzylic, maleic, succinic, chioromandelic, glutamic, nitrilotriacetic, boric, adipic, formic, glucuronic, benzoyl formic, phthalic, ketopimelic, ethyl N-(hydroxyethyl) ethylenediamine triacetic acids, alanine, serine, tryptophan, tyrosine, bicine, tricine and glycine.

23. A composition as defined in claim 22, further comprising an effective amount of a bactericide.

24. A composition as defined in claim 22, which further comprises a divalent cation chelator, and wherein said acid is selected from the group consisting of mandelic, 2-ketoglutaric, iminodiacetic, mucic, glycolic, fumaric, lactic, aspartic, phosphoric, pyruvic, citric chloroacetic acids and alanine.

25. A composition as defined in claim 24, which achieves a final concentration of 0.5% CPC, EDTA at least 0.25% and 0.1–1% of said acid.

* * * * *